(12) United States Patent
Jaroch et al.

(10) Patent No.: US 7,238,707 B2
(45) Date of Patent: *Jul. 3, 2007

(54) SUBSTITUTED PENTANOLS, A PROCESS FOR THEIR PRODUCTION AND THEIR USE AS ANTI-INFLAMMATORY AGENTS

(75) Inventors: Stefan Jaroch, Berlin (DE); Stefan Baeurle, Berlin (DE); Markus Berger, Berlin (DE); Konrad Krolikiewicz, Berlin (DE); Duy Nguyen, Berlin (DE); Hartmut Rehwinkel, Berlin (DE); Norbert Schmees, Berlin (DE); Werner Skuballa, Berlin (DE); Heike Schaecke, Berlin (DE)

(73) Assignee: Schering AG, Berlin (DE)

( * ) Notice: Subject to any disclaimer, the term of this patent is extended or adjusted under 35 U.S.C. 154(b) by 365 days.

This patent is subject to a terminal disclaimer.

(21) Appl. No.: 10/957,742

(22) Filed: Oct. 5, 2004

(65) Prior Publication Data

US 2005/0143415 A1 Jun. 30, 2005

Related U.S. Application Data

(60) Provisional application No. 60/510,091, filed on Oct. 10, 2003.

(30) Foreign Application Priority Data

Oct. 6, 2003 (DE) ................. 103 46 940

(51) Int. Cl.
*A61K 31/47* (2006.01)
*A61K 31/44* (2006.01)
*C07D 217/22* (2006.01)
*C07D 215/38* (2006.01)

(52) U.S. Cl. .............. 514/310; 514/313; 546/143; 546/159

(58) Field of Classification Search .............. 514/310, 514/313; 546/143, 159
See application file for complete search history.

(56) References Cited

U.S. PATENT DOCUMENTS

| | | | |
|---|---|---|---|
| 6,323,199 B1 | 11/2001 | Lehmann et al. | |
| 6,897,224 B2 * | 5/2005 | Jaroch et al. | ........ 514/312 |
| 2002/0077356 A1 | 6/2002 | Jaroch et al. | |
| 2004/0116694 A1 | 6/2004 | Jaroch et al. | |

FOREIGN PATENT DOCUMENTS

WO  WO 03/082827  10/2003

* cited by examiner

*Primary Examiner*—D. Margaret Seaman
(74) *Attorney, Agent, or Firm*—Millen, White, Zelano & Branigan, P.C.

(57) ABSTRACT

The invention relates to substituted pentanols, a process for their production and their use as anti-inflammatory agents.

17 Claims, No Drawings

SUBSTITUTED PENTANOLS, A PROCESS FOR THEIR PRODUCTION AND THEIR USE AS ANTI-INFLAMMATORY AGENTS

This application claims the benefit of the filing date of U.S. Provisional Application Ser. No. 60/510,091 filed Oct. 10, 2003 which is incorporated by reference herein.

The invention relates to quinoline and isoquinoline derivatives, a process for their production and their use as anti-inflammatory agents.

From the prior art of DE 100 38 639 and WO02/10143, anti-inflammatory agents of general formula

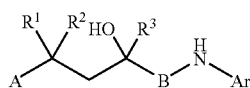

are known, whereby the Ar radical comprises phthalides, thiophthalides, benzoxazinones or phthalazinones. In the experiment, these compounds show dissociations of action between anti-inflammatory and undesirable metabolic actions and are superior to the previously described nonsteroidal glucocorticoids or exhibit at least just as good an action.

The selectivity of the compounds of the prior art compared to the other steroid receptors still requires improvement, however.

It was therefore the object of this invention to make available compounds whose selectivity is improved compared to the other steroid receptors.

This object is achieved by the compounds according to the claims.

This invention therefore relates to compounds of general formula I

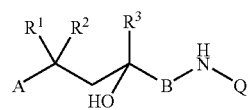

in which

A stands for an aryl, a benzyl or a phenethyl group, whereby the aryl, benzyl or phenethyl group optionally can be substituted by one or more radicals from the group $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, —O—$(CH_2)_n$—O—, —O—$(CH_2)_n$—$CH_2$—, —O—CH=CH—, or —$(CH_2)_{n+2}$—, whereby n=1 or 2, and the terminal oxygen atoms and/or carbon atoms are linked to directly adjacent ring-carbon atoms, or $NR^4R^5$, whereby $R^4$ and $R^5$, independently of one another, can be hydrogen, $C_1$-$C_5$-alkyl or (CO)—$C_1$-$C_5$-alkyl, $R^1$ and $R^2$, independently of one another, mean a hydrogen atom, a methyl or ethyl group, or together with the carbon atom mean the chain of a $C_3$-$C_6$-cycloalkyl ring, $R^3$ means an optionally substituted group that is selected from $C_4$-$C_8$-alkyl, $C_2$-$C_6$-alkenyl, $C_2$-$C_6$-alkinyl, $C_3$-$C_8$-cycloalkyl, $C_3$-$C_7$-heterocyclyl, aryl, heteroaryl, ($C_1$-$C_8$-alkyl)$C_3$-$C_8$-cycloalkyl, ($C_1$-$C_8$-alkyl)aryl, or ($C_1$-$C_8$-alkyl) heteroaryl, B means a methylene group or a carbonyl group that is optionally substituted by a methyl or ethyl group, and Q means a quinolinyl or isoquinolinyl group that is linked via any position and that optionally can be substituted by one or more radicals from the group $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, or $NR^4R^5$, whereby $R^4$ and $R^5$, independently of one another, can be hydrogen, $C_1$-$C_5$-alkyl or (CO)-$C_1$-$C_5$-alkyl, as well as their racemates or separately present stereoisomers, and optionally their physiologically compatible salts.

An aryl group comprises phenyl and naphthyl. Phenyl is preferred.

The substituted aryl, benzyl or phenethyl groups carry 1-3 substituents, preferably 2 substituents, on the ring.

The following substitution patterns on ring A are a special subject of the invention: 2,5-disubstituted phenyl derivatives and 2,4-disubstituted phenyl derivatives.

The $C_1$-$C_5$-alkyl groups in A, $R^4$, and $R^5$ can be straight-chain or branched and stand for a methyl, ethyl, n-propyl, iso-propyl, n-butyl, iso-butyl, tert.-butyl- or n-pentyl, 2,2-dimethylpropyl, 2-methylbutyl or 3-methylbutyl group. A methyl or ethyl group is preferred.

The $C_4$-$C_8$-alkyl group $R^3$ can be straight-chain or branched and can mean, e.g., butyl, isobutyl, tert-butyl, pentyl or isopentyl.

The $C_2$-$C_6$-alkenyl group is straight-chain or branched; for example, vinyl, propenyl, isopropenyl, butenyl, or isobutenyl is suitable.

The $C_2$-$C_6$-alkinyl group is straight-chain or branched; for example, ethinyl, propinyl, or butinyl is suitable.

For a cycloalkyl group, for example, cyclobutyl, cyclopentyl, cyclohexyl, cycloheptyl, and cyclooctyl are considered.

The heterocyclyl group is not aromatic and can be, for example, pyrrolidine, imidazolidine, pyrazolidine, or piperidine.

The $C_1$-$C_8$-alkyl($C_3$-$C_8$)cycloalkyl group can be, for example, cyclobutylmethyl, cyclopentylmethyl, cyclohexylmethyl, or cycloheptylmethyl. The linkage with the chain is carried out via the alkyl group.

For an aryl group, phenyl and naphthyl are considered, and for ($C_1$-$C_8$)alkylaryl, benzyl and homobenzyl are considered.

Heteroaryl comprises furanyl, thienyl, thiazolyl, oxazolyl, imidazolyl, triazolyl, pyridyl and pyrimidyl;

($C_1$-$C_8$-Alkyl)heteroaryl comprises all combinations of the above-indicated definition of alkyl with monocyclic aromatic heterocyclic compounds. The linkage with the chain is carried out via the alkyl group, which in turn is linked to any possible chemical position of the heterocyclic compound.

The substituents of the groups in $R^3$ can be $C_1$-$C_6$-alkyl, $C_2$-$C_6$-alkenyl, $C_2$-$C_6$-alkinyl, $C_1$-$C_6$-alkoxy, halogen, hydroxy, and $NR^4R^5$.

Alkyl radicals $R^1$ and $R^2$ together with the carbon atom of the chain can form a 3-to 6-membered ring.

The $C_1$-$C_5$-alkoxy groups in A and Q can be straight-chain or branched and stand for a methoxy, ethoxy, n-propoxy-, iso-propoxy-, n-butoxy, iso-butoxy, tert.-butoxy or n-pentoxy, 2,2-dimethylpropoxy, 2-methylbutoxy or 3-methylbutoxy group. A methoxy or ethoxy group is preferred.

The $C_1$-$C_5$-alkylthio groups in A and Q can be straight-chain or branched and stand for a methylthio, ethylthio, n-propylthio, iso-propylthio, n-butylthio, iso-butylthio, tert.- butylthio or n-pentylthio, 2,2-dimethylpropylthio, 2-methylbutylthio or 3-methylbutylthio group. A methylthio or ethylthio group is preferred.

The designation halogen atom or halogen means a fluorine, chlorine, bromine or iodine atom. A fluorine, chlorine or bromine atom is preferred.

The $NR^4R^5$ group can mean, for example, $NH_2$, $N(H)CH_3$, $N(CH_3)_2$, $N(H)(CO)CH_3$, $N(CH_3)(CO)CH_3$, $N[(CO)CH_3]_2$, $N(H)CO_2CH_3$, $N(CH_3)CO_2CH_3$, or $N(CO_2CH_3)_2$.

As alkyl radicals $R^4$ and $R^5$, $C_1$-$C_3$-alkyl is preferred.

As acyl radicals $R^4$ and $R^5$, $(CO)$—$C_1$-$C_3$-alkyl is preferred.

For radical B, the unsubstituted methylene group and the carbonyl group are preferred.

Radical Q can be linked via any ring-carbon atom to the (NH)-group of the chain. 4-, 5- and 8-positions are preferred for the quinoline ring, and 1-position is preferred for the isoquinoline ring.

The compounds of general formula I according to the invention can be present as different stereoisomers because of the presence of asymmetry centers. Both the racemates and the separately present stereoisomers are part of the subject of this invention.

A special subject of this invention are the separately present stereoisomers, i.e., (+)-enantiomers and (−)-enantiomers.

Another subject of the invention relates to compounds in which A stands for an aryl, a benzyl or a phenethyl group, whereby the aryl, benzyl or phenethyl group optionally can be substituted by one or more radicals from the group $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro or $NR^4R^5$, whereby $R^4$ and $R^5$, independently of one another, can be hydrogen, $C_1$-$C_5$-alkyl or $(CO)$—$C_1$-$C_5$-alkyl.

Another subject of the invention relates to compounds of general formula I, in which A stands for —O—$(CH_2)_n$—O—, —O—$(CH_2)_n$—$CH_2$—, —O—CH=CH—, or —$(CH_2)_{n+2}$—, whereby n=1 or 2, and the terminal oxygen atoms and/or carbon atoms are linked to directly adjacent ring-carbon atoms.

Compounds according to claim 1, in which $R^3$ means an optionally substituted group that is selected from $C_4$-$C_8$-alkyl, $C_3$-$C_8$-cycloalkyl, $C_3$-$C_7$-heterocyclyl, aryl, heteroaryl, $(C_1$-$C_8$-alkyl)$C_3$-$C_8$-cycloalkyl, $(C_1$-$C_8$-alkyl)aryl, or $(C_1$-$C_8$-alkyl)heteroaryl, are another subject of the invention.

Compounds according to claim 1, in which $R^3$ means an optionally substituted group that is selected from $C_3$-$C_6$-cycloalkyl, $C_3$-$C_7$-heterocyclyl, phenyl, heteroaryl, $(C_1$-$C_3$-alkyl)$C_3$-$C_6$-cycloalkyl, $(C_1$-$C_3$-alkyl)phenyl, or $(C_1$-$C_3$-alkyl)heteroaryl, are another subject of the invention.

Compounds of general formula I, in which A means an unsubstituted phenyl group, $R^1$ and $R^2$ mean methyl, $R^3$ means a cyclopentyl group, a methylcyclohexyl group or a phenyl group, B means a methylene group and Q means a quinoline or isoquinoline group, are another subject of the invention.

Compounds of general formula I, in which A means an unsubstituted phenyl group, $R^1$ and $R^2$ mean a methyl group, $R^3$ means a cyclopentyl group, a methylcyclohexyl group or a phenyl group, B means a methylene group and Q means a quinoline group, are another subject of the invention.

In addition, subjects of the invention are the use of the compounds according to claim 1 for the production of pharmaceutical agents, the use of the compounds according to claim 1 for the production of a pharmaceutical agent for treating inflammatory diseases and pharmaceutical preparations that contain at least one compound according to claim 1 or their mixtures as well as pharmaceutically compatible vehicles.

Compounds of general formula I in which $R^3$ means $C_3$-$C_8$-cycloalkyl, $(C_1$-$C_8$alkyl)$C_3$-$C_8$-cycloalkyl, benzyl or phenyl are a preferred subject of the invention.

Compounds of general formula I in which $R^3$ means $C_3$-$C_8$-cycloalkyl, $(C_1$-$C_8$alkyl)$C_3$-$C_8$-cycloalkyl, or phenyl are an especially preferred subject of the invention, and compounds of general formula I in which $R^3$ means cyclopentyl, methylcyclohexyl or phenyl, as described in the examples, are quite especially preferred.

The process for the production of the compounds of WO98/54159 (51488), WO00/32584 (51642), and WO02/10143 (51877) can also be used for the production of the compounds according to the invention. For the linkage of the quinoline or isoquinoline groups that are characteristic of the compounds according to the invention, the following process steps can be performed:

A1)

for B = CO

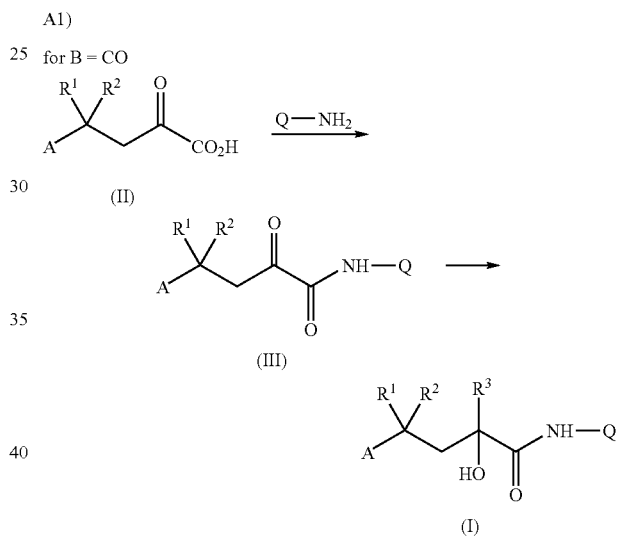

An α-keto acid of general formula (II), in which A, $R^1$ and $R^2$ have the meanings that are indicated for formula (I), is converted with an aminoquinoline, an aminoisoquinoline or a (partially-) hydrogenated quinoline or isoquinoline derivative ($Q$-$NH_2$) into α-ketoamide (III), whereby A, $R^1$ and $R^2$ have the above-indicated meanings, in the way that is known to one skilled in the art. For example, α-ketoamide (III) is obtained with use of dehydrating coupling reagents, as they are known from peptide chemistry, e.g., dicyclohexylcarbodiimide, or by upstream conversion of the acid into an acid chloride, e.g., with thionyl chloride or $POCl_3$ and subsequent reaction with $Q$-$NH_2$.

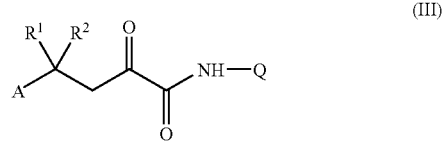

Compound (III) is reacted either with an alkyl metal compound, for example a Grignard reagent, or a lithium alkyl, or by reaction with compound (IV),

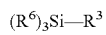    (IV)

whereby $R^3$ has the above-indicated meaning, and $R^6$ refers to a $C_1$-$C_5$-alkyl group, in the presence of a catalyst, e.g., fluoride salts or bases, such as, for example, alkali carbonates (*J. Am. Chem. Soc.* 1989, 111, 393), to form title compound (I).

A2)

for B = CO

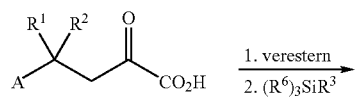

(II)

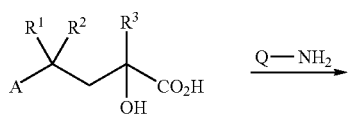

(VI)

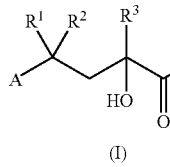

(I)

[Key: verestern = esterification]

As an alternative, α-keto acids (II) can also be esterified to compounds (V),

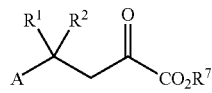

(V)

in which A, $R^1$ and $R^2$ are defined as described above, and $R^7$ is $C_1$-$C_4$-alkyl, according to commonly used methods, e.g., with thionyl chloride in methanol or ethanol or with methyl iodide and alkali carbonate, and can be converted from (III) to (I) in compound (VI) analogously to reaction sequence A1).

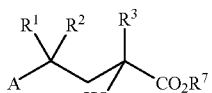

(VI)

The ester is saponified under standard conditions, for example aqueous alkali hydroxide solution, to acid (VI; $R^7$=H). The latter is reacted for coupling with an aminoquinoline or aminoisoquinoline or a (partially-) hydrogenated quinoline or isoquinoline derivative (Q-$NH_2$) with use of a conventional activating reagent, e.g., thionyl chloride, optionally in the presence of a catalyst such as dimethyl aminopyridine, to form title compound (I).

B)

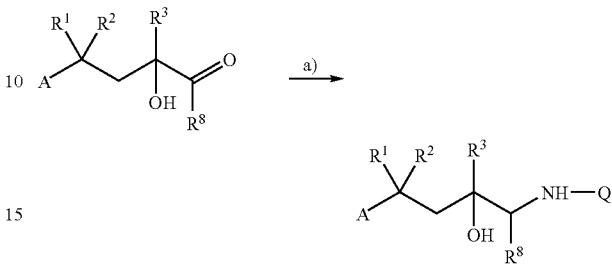

Title compound (I) can also be synthesized by reductive amination of a compound of formula (XII) with Q-$NH_2$, whereby, e.g., sodium cyanoborohydride, or sodium triacetoxy borohydride is considered as a reducing agent.

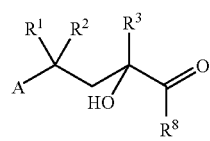

(XII)

$R^8$ means methyl or ethyl according to the substituents that are defined for the methylene group in B.

In the case that the compounds of general formula I are present as salts, this can be, for example, in the form of hydrochloride, sulfate, nitrate, phosphate, pivalate, maleate, fumarate, tartrate, benzoate, mesylate, citrate or succinate.

If the compounds according to the invention are present as racemic mixtures, they can be separated into pure, optically active forms according to the methods of racemate separation that are familiar to one skilled in the art. For example, the racemic mixtures can be separated by chromatography on an even optically active carrier material (CHIRALPAK AD®) into the pure isomers. It is also possible to esterify the free hydroxy group in a racemic compound of general formula I with an optically active acid and to separate the diastereoisomeric esters that are obtained by fractionated crystallization or by chromatography, and to saponify the separated esters in each case to the optically pure isomers. As an optically active acid, for example, mandelic acid, camphorsulfonic acid or tartaric acid can be used.

Moreover, the methods for the production of the compounds according to the invention that are used in the experimental part are also part of the disclosure for the producibility of the claimed compounds.

The binding of the substances to the glucocorticoid receptor (GR) and other steroid hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses, which code for the GR, are used for the binding studies. In comparison to reference substance [$^3$H]-dexamethasone, the substances show a high to very high affinity to GR.

Moreover, the quinolines and isoquinolines of formula (I) that are described here show a high selectivity for the glucocorticoid receptor.

As an essential, molecular mechanism for the anti-inflammatory action of glucocorticoids, the GR-mediated inhibition of the transcription of cytokines, adhesion molecules, enzymes and other pro-inflammatory factors is considered. This inhibition is produced by an interaction of the GR with other transcription factors, e.g., AP-1 and NF-kappa-B (for a survey, see Cato, A. C. B. and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits.

The anti-inflammatory action of the compounds of general formula I was tested in the animal experiment by tests in the croton oil-induced inflammation in rats and mice (J. Exp. Med. (1995), 182, 99-108). To this end, croton oil in ethanolic solution was applied topically to the animals' ears. The test substances were also applied topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf., Hatz, H. J., Glucocorticoide: Immunologische Grundlagen, Pharmakologie und Therapierichtlinien, [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses in which they have an anti-inflammatory action, the compounds of general formula I induce little or no tyrosinamino transferase.

Because of their anti-inflammatory and, in addition, antiallergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:
Chronic, obstructive lung diseases of any origin, primarily bronchial asthma
Bronchitis of different origins
All forms of restrictive lung diseases, primarily allergic alveolitis,
All forms of pulmonary edema, primarily toxic pulmonary edema
Sarcoidoses and granulomatoses, especially Boeck's disease (ii) Rheumatic diseases/autoimmune diseases/joint diseases that are accompanied by inflammatory, allergic and/or proliferative processes:
All forms of rheumatic diseases, especially rheumatoid arthritis, acute rheumatic fever, polymyalgia rheumatica
Reactive arthritis
Inflammatory soft-tissue diseases of other origins
Arthritic symptoms in the case of degenerative joint diseases (arthroses)
Traumatic arthritides
Collagenoses of any origin, e.g., systemic lupus erythematodes, sclerodermia, polymyositis, dermatomyositis, Sjögren's syndrome, Still's syndrome, Felty's syndrome (iii) Allergies that are accompanied by inflammatory and/or proliferative processes:
All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (vasculitides)
Panarteritis nodosa, temporal arteritis, erythema nodosum (v) Dermatological diseases that are accompanied by inflammatory, allergic and/or proliferative processes:
Atopic dermatitis (primarily in children)
Psoriasis
Pityriasis rubra pilaris
Erythematous diseases, triggered by different noxae, e.g., radiation, chemicals, burns, etc.
Bullous dermatoses
Diseases of the lichenoid group,
Pruritis (e.g., of allergic origin)
Seborrheal eczema
Rosacea
Pemphigus vulgaris
Erythema exudativum multiforme
Balanitis
Vulvitis
Hair loss such as alopecia areata
Cutaneous T-cell lymphoma (vi) Kidney diseases that are accompanied by inflammatory, allergic and/or proliferative processes:
Nephrotic syndrome
All nephritides (vii) Liver diseases that are accompanied by inflammatory, allergic and/or proliferative processes:
Acute liver cell decomposition
Acute hepatitis of different origins, e.g., viral, toxic, pharmaceutical agent-induced
Chronic aggressive hepatitis and/or chronic intermittent hepatitis (viii) Gastrointestinal diseases that are accompanied by inflammatory, allergic and/or proliferative processes:
Regional enteritis (Crohn's disease)
Colitis ulcerosa
Gastritis
Reflux esophagitis
Ulcerative colitis of other origins, e.g., native sprue (ix) Proctologic diseases that are accompanied by inflammatory, allergic and/or proliferative processes:
Anal eczema
Fissures Hemorrhoids
Idiopathic proctitis
(x) Eye diseases that are accompanied by inflammatory, allergic and/or proliferative processes:
Allergic keratitis, uveitis, iritis
Conjunctivitis
Blepharitis
Optic neuritis
Chorioiditis
Sympathetic ophthalmia
(xi) Diseases of the ear-nose-throat area that are accompanied by inflammatory, allergic and/or proliferative processes:
Allergic rhinitis, hay fever
Otitis externa, e.g., caused by contact dermatitis, infection, etc.
Otitis media
(xii) Neurological diseases that are accompanied by inflammatory, allergic and/or proliferative processes:
Cerebral edema, primarily tumor-induced cerebral edema
Multiple sclerosis
Acute encephalomyelitis
Meningitis
Various forms of convulsions, e.g., infantile nodding spasms
(xiii) Blood diseases that are accompanied by inflammatory, allergic and/or proliferative processes:
Acquired hemolytic anemia
Idiopathic thrombocytopenia
(xiv) Tumor diseases that are accompanied by inflammatory, allergic and/or proliferative processes:
Acute lymphatic leukemia
Malignant lymphoma
Lymphogranulomatoses
Lymphosarcoma
Extensive metastases, mainly in breast, bronchial and prostate cancers
(xv) Endocrine diseases that are accompanied by inflammatory, allergic and/or proliferative processes:
Endocrine orbitopathy
Thyreotoxic crisis
De Quervain's thyroiditis
Hashimoto's thyroiditis
Basedow's disease
(xvi) Organ and tissue transplants, graft-versus-host disease
(xvii) Severe shock conditions, e.g., anaphylactic shock, systemic inflammatory response syndrome (SIRS)
(xviii) Substitution therapy in:
Innate primary suprarenal insufficiency, e.g., congenital adrenogenital syndrome
Acquired primary suprarenal insufficiency, e.g., Addison's disease, autoimmune adrenalitis, meta-infective tumors, metastases, etc.
Innate secondary suprarenal insufficiency, e.g., congenital hypopituitarism
Acquired secondary suprarenal insufficiency, e.g., meta-infective tumors, etc.
(xix) Vomiting that is accompanied by inflammatory, allergic and/or proliferative processes:
e.g., in combination with a 5-HT3 antagonist in cytostatic-agent-induced vomiting
(xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie und Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

In addition, the invention provides:
(i) The use of one of the compounds of general formula I according to the invention or mixture thereof for the production of a medication for treating a DISEASE;
(ii) A process for treating a DISEASE, said process comprises an administration of an amount of the compound according to the invention, whereby the amount suppresses the disease and whereby the amount of compound is given to a patient who requires such a medication;
(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 µg to 100,000 µg of the compound according to the invention per kg of body weight. In the case of larger mammals, for example the human, a recommended daily dose lies in the range of 1 µg to 100,000 µg per kg of body weight. Preferred is a dose of 10 to 30,000 µg per kg of body weight, and more preferred is a dose of 10 to 10,000 µg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles that are commonly used in galenicals, fillers, substances that influence decomposition, binding agents, moisturizers, lubricants, absorbents, diluents, flavoring correctives, coloring agents, etc., and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

The examples below are used for a more detailed explanation of the invention without intending that it be limited thereto. The syntheses of important precursors, which are not disclosed within the scope of the experiments, are already prior art and can be derived from, for example, WO 98/54159 and WO 02/10143.

Experiments

EXAMPLE 1

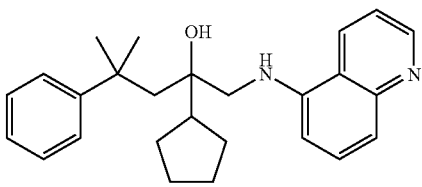

1-(Quinolin-5-ylamino)-2-cyclopentyl-4-methyl-4-phenylpentan-2-ol

4-Methyl-4-phenyl-2-oxopentanoic Acid-ethyl Ester 10.0 g of 2-phenyl-2-propanol and 30.4 g of 2-(trimethylsilyloxy)acrylic acid-ethyl ester (*Bull. Chem. Soc. Jpn.* 1992, 65, 3209) are introduced into 386 ml of $CH_2Cl_2$ and treated at −70° C. with 11.5 ml of tin tetrachloride. After 15 minutes at −70° C., the batch is introduced into semiconcentrated potassium carbonate solution, extracted with $CH_2Cl_2$, dried ($Na_2SO_4$) and concentrated by evaporation in a vacuum. Column chromatography on silica gel with ethyl acetate-cyclohexane yields 4.64 g of the product as a colorless oil.

$^1$H-NMR ($CDCl_3$); δ=1.23 (t, 3H), 1.45 (s, 6H), 3.16 (s, 2H), 4.09 (q, 2H), 7.14-7.40 (m, 5H).

2-Cyclopentyl-2-hydroxy-4-methyl-4-phenylpentanoic Acid-ethyl Ester 2.13 ml of a 2 M ethereal cyclopentyl magnesium chloride solution is added in drops at −70° C. to a solution of 1.0 g of 4-methyl-4-phenyl-2-oxopentanoic acid-ethyl ester in 20 ml of THF. After 3 hours at −70° C., the batch is poured into cold, saturated $NH_4Cl$ solution and extracted with ethyl acetate. The extracts are dried ($Na_2SO_4$) and concentrated by evaporation. Column chromatography on silica gel with ethyl acetate-cyclohexane yields 320 mg of the product.

$^1$H-NMR ($CDCl_3$); δ=0.90-1.80 (m, 8H), 1.15 (t, 3H), 1.34 (s, 3H), 1.43 (s, 3H), 2.09 (m, 1H), 2.14 (d, 1H), 2.26 (d, 1H), 2.84 (s, 1H), 3.50 (dt, 1H), 7.13 (m, 1H), 7.20-7.48 (m, 4H).

2-Cyclopentyl-4-methyl-4-phenyl-12-pentanediol 320 mg of 2-cyclopentyl-2-hydroxy-4-methyl-4-phenylpentanoic acid-ethyl ester is converted with 92 mg of lithium aluminum hydride into 185 mg of product.

$^1$H-NMR ($CDCl_3$); δ=1.10-1.70 (m, 8H), 1.40 (s, 3H), 1.49 (s, 3H), 2.00 (AB system, 2H), 2.08 (m, 1H), 3.18 (AB system, 2H), 7.20 (t, 1H), 7.32 (t, 2H), 7.45 (d, 2H).

2-Cyclopentyl-2-hydroxy-4-methyl-4-phenylpentanal 185 mg of 2-cyclopentyl-4-methyl-4-phenyl-1,2-pentanediol is converted with 438 mg of pyridine-sulfur trioxide complex, 2.5 ml of DMSO and 0.5 ml of triethylamine into 160 mg of aldehyde.

$^1$H-NMR ($CDCl_3$); δ=0.70-1.70 (m, 9H), 1.30 (s, 3H), 1.40 (s, 3H), 2.11 (d, 1H), 2.29 (d, 1H), 3.02 (s, 1H), 7.20 (m, 1H), 7.30 (m, 4H), 8.85 (s, 1H).

1-(Quinolin-5-ylamino)-2-cyclopentyl-4-methyl-4-phenylpentan-2-ol 160 mg of 2-cyclopentyl-2-hydroxy-4-methyl-4-phenylpentanal, 106 mg of 5-aminoquinoline and 405 mg of sodium triacetoxy borohydride in 6.3 ml of acetic acid are converted into imine.

$^1$H-NMR ($CDCl_3$); δ=0.80-1.70 (m, 15H), 2.75 (d, 1H), 3.01 (d, 1H), 3.87 (m, 1H), 4.81 (d, 1H), 6.12 (d, 1H), 7.15-7.50 (m, 8H), 8.20 (d, 1H), 8.88 (dd, 1H).

MS (ESI), 387.

Column chromatography on silica gel with ethyl acetate-cyclohexane yields 70 mg of imine, which is reduced with 21 mg of sodium borohydride in THF (2 ml) and methanol (0.5 ml). Column chromatography yields 30 mg of product.

$^1$H-NMR ($CDCl_3$); δ=0.80-2.00 (m, 17H), 3.30 (m, 1H), 3.73 (m, 1H), 5.90 (d, 1H), 7.25-7.40 (m, 8H), 8.10 (d, 1H), 8.77 (dd, 1H).

MS (ESI), 389.

EXAMPLE 2

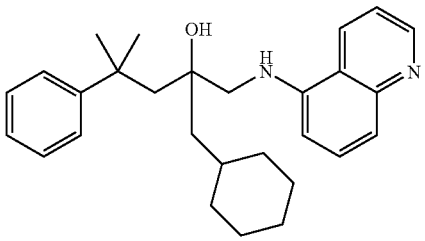

1-(Quinolin-5-ylamino)-2-cyclohexylmethyl-4-methyl-4-phenylpentan-2-ol

2-Cyclohexylmethyl-2-hydroxy-4-methyl-4-phenyl-pentanoic Acid-ethyl Ester

Analogously to Example 1, 1.0 g of 4-methyl-4-phenyl-2-oxopentanoic acid-ethyl ester is converted with Grignard reagent that is produced from 1 ml of cyclohexylmethyl bromide and 174 mg of magnesium into 290 mg of product.
'H-NMR (CDCl$_3$); δ=0.70-1.75 (m, 13H), 1.25 (t, 3H), 1.31 (s, 3H), 1.40 (s, 3H), 2.03 (d, 1H), 2.26 (d, 1H), 3.50 (dt, 1H), 3.90 (dt, 1H), 7.15 (t, 1H), 7.22-7.36 (m, 4H).

2-Cyclohexylmethyl-4-methyl-4-phenyl-1,2-pentanediol

Analogously to Example 1, 290 mg of 2-cyclohexylmethyl-2-hydroxy-4-methyl-4-phenylpentanoic acid-ethyl ester is converted with 76 mg of lithium aluminum hydride into 160 mg of product.
'H-NMR (CDCl$_3$); δ=0.90 (m, 3H), 1.10-1.80 (m, 10H), 1.40 (s, 3H), 1.43 (s, 3H), 1.94 (d, 1H), 2.10 (d, 1H), 3.12 (AB system, 2H), 7.20 (t, 1H), 7.32 (t, 2 H), 7.43 (d, 2H).

1-(Quinolin-5-ylamino)-2-cyclohexylmethyl-4-methyl-4-phenylpentan-2-ol

Analogously to Example 1, 160 mg of 2-cyclohexylmethyl-4-methyl-4-phenyl-1,2-pentanediol is reacted with 342 mg of pyridine-sulfur trioxide complex, 1.95 ml of DMSO and 0.39 ml of triethylamine to form 2-cyclohexylmethyl-2-hydroxy-4-methyl-4-phenylpentanal ('H-NMR (CDCl$_3$); δ=0.90-1.60 (m, 10H), 1.30 (s, 3H), 1.41 (s, 3H), 1.76 (m, 2H), 1.95 (m, 1H), 2.20 (d, 1H), 2.35 (d, 1H), 2.97 (s, 1H), 7.20 (m, 1H), 7.30 (m, 4H), 8.76 (s, 1H)). The crude product is reacted with 137 mg of 5-aminoquinoline and 524 mg of sodium triacetoxy borohydride to form imine (180 mg; 'H-NMR (CDCl$_3$); δ=0.90-1.90 (m, 18H), 2.25 (m, 1H), 2.80 (d, 1H), 3.00 (d, 1 H), 3.76 (t, 1H), 5.06 (d, 1H), 6.25 (d, 1H), 7.10-7.55 (m, 8H), 8.25 (d, 1H), 8.87 (dd, 1H); MS (ESI), 415). Reductive amination with 49 mg of sodium borohydride yields 130 mg of end product after column chromatography.
'H-NMR (CDCl$_3$); δ=1.10-1.90 (m, 20H), 2.12 (m, 1H), 3.41 (m, 1H), 3.70 (m, 1H), 4.31 (m, 1H), 6.47 (dd, 1H), 7.20-7.45 (m, 8H), 8.07 (d, 1H), 8.82 (dd, 1H).
MS (ESI), 417.

EXAMPLE 3

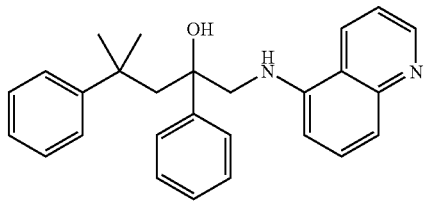

1-(Quinolin-5-ylamino)-2,4-diphenyl-4-methylpentan-2-ol

2,4-Diphenyl-2-hydroxy-4-methylpentanoic Acid-ethyl Ester

Analogously to Example 1, 1.0 g of 4-methyl-4-phenyl-2-oxopentanoic acid-ethyl ester is converted with 2.14 ml of a 2 M phenylmagnesium chloride-THF solution into 980 mg of product.

2,4-Diphenyl-4-methyl-1,2-pentanediol

Analogously to Example 1, 980 mg of diphenyl-2-hydroxy-4-methylpentanoic acid-ethyl ester is converted with 289 mg of lithium aluminum hydride into 450 mg of product.
'H-NMR (CDCl$_3$); δ=1.10 (s, 3H), 1.25 (s, 3H), 2.23 (d, 1H), 2.61 (d, 1H), 3.41 (AB-System, 2H), 7.15-7.37 (m, 10H).

2,4-Diphenyl-2-hydroxy-4-methylpentanal

Analogously to Example 1, 445 mg of 2,4-diphenyl-4-methyl-1,2-pentanediol is converted with 1.02 g of pyridine-sulfur trioxide complex, 5.85 ml of DMSO and 1.16 ml of triethylamine into 390 mg of aldehyde.
'H-NMR (CDCl3); δ=1.36 (s, 3H), 1.51 (s, 3H), 2.49 (d, 1H), 2.82 (d, 1H), 3.60 (s, 1H), 7.20-7.42 (m, 10H), 8.98 (s, 1H).

1-(Quinolin-5-ylamino)-2,4-diphenyl-4-methylpentan-2-ol

Analogously to Example 1, 40 mg of product is obtained from 190 mg of 2,4-diphenyl-2-hydroxy-4-methylpentanal and 122 mg of 5-aminoquinoline via the imine ('H-NMR (CDCl$_3$); δ=1.37 (d, 3H), 1.42 (s, 3H), 2.70 (d, 1H), 2.94 (d, 1H), 4.67 (s,1H), 6.14 (d, 1H), 6.22 (br., 1H), 7.12-7.40 (m, 13H), 8.34 (d, 1H), 8.85 (dd, 1H)).
'H-NMR ([D$_6$]-DMSO); δ=1.24 (s, 3H), 1.35 (s, 3H), 1.50 & 1.78 (dd, 1H), 2.00 (m, 1H), 3.59 & 3.80 (m, 1H), 4.18 & 4.30 (m, 1H), 4.86 (m, 1H), 6.13-6.30 (m2H), 7.09-7.33 (m, 10H), 7.39 (d, 1H), 7.54 (dd, 1H), 8.68 (d, 1H), 8.81 (d, 1H).

The invention claimed is:
1. A compound of formula I

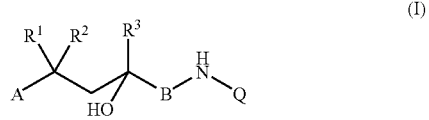

in which
A stands for an aryl, a benzyl or a phenethyl group, wherein the aryl, benzyl or phenethyl group is optionally substituted by one or more of $C_1$-$C_5$-alkyl, $C_1$-$C_5$-alkoxy, $C_1$-$C_5$alkylthio, $C_1$-$C_5$-perfluoroalkyl, halogen, hydroxy, cyano, nitro, —O—(CH$_2$)$_n$—O—, —O—(CH$_2$)$_n$—CH$_2$—, —O—CH=CH—, or —(CH$_2$)$_{n+2}$—, wherein n=1 or 2, and the terminal oxygen atoms and/or carbon atoms are linked to directly adjacent ring-carbon atoms, or NR$^4$R$^5$,
R$^4$ and R$^5$ are, independently of one another, hydrogen, $C_1$-$C_5$-alkyl or (CO)—$C_1$-$C_5$-alkyl, R¹ and R² are, independently of one another, a hydrogen atom, a methyl or ethyl group, or together with the carbon atom to which they are attached mean the chain of a $C_3$-$C_6$-cycloalkyl ring, R³ means an optionally substituted group that is $C_4$-$C_8$-alkyl, $C_2$-$C_6$-alkenyl, $C_2$-$C_6$-alkinyl, $C_3$-$C_8$-cycloalkyl, $C_3$-$C_7$-heterocyclyl, aryl, heteroaryl, ($C_1$-$C_8$-alkyl)$C_3$-$C_8$-cycloalkyl, ($C_1$-$C_8$-alkyl)aryl, or ($C_1$-$C_8$-alkyl) heteroaryl, B means a methylene group or a carbonyl group that is optionally substituted by a methyl or ethyl group, and Q means a quinolinyl or isoquinolinyl group that is linked via any position and that is optionally substituted by one or more of $C_1$-$C_5$-alkyl, $C_1$-$C_5$-alkoxy, $C_1$-$C_5$-alkylthio, $C_1$-$C_5$-perfluoroalkyl, halogen, hydroxy, cyano, nitro, or $NR^4R^5$, or a racemate or separated isomer thereof, of a pharmaceutically acceptable salt thereof.

2. A compound according to claim 1, in which A stands for an aryl group.

3. A compound according to claim 1, in which A means —O—$(CH_2)_n$—O—, —O—$(CH_2)_n$—$CH_2$—, —O—CH=CH—, or —$(CH_2)_{n+2}$—, wherein n=1 or 2, and the terminal oxygen atoms and/or carbon atoms are linked to directly adjacent ring-carbon atoms.

4. A compound according to claim 1, in which R³ means an optionally substituted $C_4$-$C_8$-alkyl, $C_3$-$C_8$-cycloalkyl, $C_3$-$C_7$-heterocyclyl, aryl, heteroaryl, ($C_1$-$C_8$-alkyl)$C_3$-$C_8$-cycloalkyl, ($C_1$-$C_8$-alkyl)aryl, or ($C_1$-$C_8$-alkyl)heteroaryl.

5. A compound according to claim 1, in which R³ means an optionally substituted $C_3$-$C_6$-cycloalkyl, $C_3$-$C_7$-heterocyclyl, phenyl, heteroaryl, ($C_1$-$C_3$-alkyl)$C_3$-$C_6$-cycloalkyl, ($C_1$-$C_3$-alkyl)phenyl or ($C_1$-$C_3$-alkyl)heteroaryl.

6. A pharmaceutical composition comprising compound according to claim 1 and a pharmaceutically acceptable vehicle.

7. A method for treating an inflammatory disease comprising administering to a patient in need thereof an effective amount of a composition according to claim 6.

8. A compound accruing to claim 1, wherein

A means an unsubstituted phenyl group,

R¹ and R² mean methyl,

R³ means a cyclopentyl group, a methylcyclohexyl group or a phenyl group,

B means a methylene group, and

Q means a quinoline or isoquinoline group.

9. A compound accruing to claim 1, wherein

A means an unsubstituted phenyl group,

R¹ and R² mean a methyl group,

R³ means a cyclopentyl group, a methylcyclohexyl group or a phenyl group,

B means a methylene group, and

Q means a quinoline group.

10. A compound accruing to claim 1, wherein R³ means $C_3$-$C_8$-cycloalkyl, ($C_1$-$C_8$alkyl)$C_3$-$C_8$-cycloalkyl, benzyl or phenyl.

11. A compound accruing to claim 1, wherein R³ means $C_3$-$C_8$-cycloalkyl, ($C_1$-$C_8$alkyl)$C_3$-$C_8$-cycloalkyl or phenyl.

12. A compound accruing to claim 1, wherein R³ means cyclopentyl, methylcyclohexyl or phenyl.

13. A compound accruing to claim 1, which is 1-(Quinolin-5-ylamino)-2-cyclopentyl-4-methyl-4-phenylpentan-2-ol, 1-(Quinolin-5-ylamino)-2-cyclohexylmethyl-4-methyl-4-phenylpentan-2-ol, or 1-(Quinolin-5-ylamino)-2,4-diphenyl-4-methylpentan-2-ol.

14. A method according to claim 7, wherein the inflammatory disease is rheumatoid arthritis.

15. A pharmaceutical composition comprising compound according to claim 13 and a pharmaceutically acceptable vehicle.

16. A method for treating an inflammatory disease comprising administering to a patient in need thereof an effective amount of a composition according to claim 15.

17. A method according to claim 16, wherein the inflammatory disease is rheumatoid arthritis.

* * * * *

UNITED STATES PATENT AND TRADEMARK OFFICE
CERTIFICATE OF CORRECTION

PATENT NO. : 7,238,707 B2  Page 1 of 1
APPLICATION NO. : 10/957742
DATED : July 3, 2007
INVENTOR(S) : Stefan Jaroch It is certified that error appears in the above-identified patent and that said Letters Patent is hereby corrected as shown below:

Column 14, line 63, reads "n=1 or 2," should read -- n = 1 or 2, --
Column 15, line 19, reads "of a pharmaceutically" should read -- or a pharmaceutically --
Column 15, line 24, reads "n=1 or 2," should read -- n = 1 or 2, --
Column 15, line 36, reads "comprising compound" should read -- comprising a compound --
Column 16, line 1, reads "A compound accruing to" should read -- A compound according to --
Column 16, line 8, reads "A compound accruing to" should read -- A compound according to --
Column 16, line 15, reads "A compound accruing to" should read -- A compound according to --
Column 16, line 16, reads "$(C_1-C_8alkyl)$" should read -- $(C_1-C_8-alkyl)$ --
Column 16, line 18, reads "A compound accruing to" should read -- A compound according to --
Column 16, line 19, reads "$(C_1-C_8alkyl)$" should read -- $(C_1-C_8-alkyl)$ --
Column 16, line 21, reads "A compound accruing to" should read -- A compound according to --
Column 16, line 23, reads "A compound accruing to" should read -- A compound according to --
Column 16, line 32, reads "comprising compound" should read -- comprising a compound --

Signed and Sealed this

Eighteenth Day of December, 2007

JON W. DUDAS
*Director of the United States Patent and Trademark Office*